United States Patent [19]

Rollband

[11] Patent Number: 5,310,402
[45] Date of Patent: * May 10, 1994

[54] TEMPORARY BANDAGE TAPE

[76] Inventor: Ernest J. Rollband, 3415 Slaterville Rd., Brooktondale, N.Y. 14817

[ * ] Notice: The portion of the term of this patent subsequent to May 25, 2010 has been disclaimed.

[21] Appl. No.: 716,903

[22] Filed: Jun. 18, 1991

Related U.S. Application Data

[63] Continuation-in-part of Ser. No. 621,261, Dec. 3, 1990, Pat. No. 5,213,565.

[51] Int. Cl.$^5$ .............................................. A61L 15/00
[52] U.S. Cl. ......................................... 602/42; 602/52; 602/55; 602/58; 602/903
[58] Field of Search ........ 128/155, 156, 169, 849-856; 604/180, 304-308

[56] References Cited

U.S. PATENT DOCUMENTS

| | | | |
|---|---|---|---|
| 1,643,926 | 9/1927 | Dickson | 128/156 |
| 2,068,703 | 1/1937 | Powdermaker . | |
| 2,133,609 | 10/1938 | Eustis . | |
| 3,878,843 | 4/1978 | Morgan | 128/851 |
| 4,005,709 | 2/1977 | Laerdal . | |
| 4,377,159 | 3/1983 | Hansen . | |
| 4,755,170 | 7/1988 | Golden . | |
| 4,807,613 | 2/1989 | Koehnke et al. . | |
| 4,966,138 | 10/1990 | Chow et al. . | |
| 4,981,133 | 1/1991 | Rollband . | |
| 5,000,172 | 3/1991 | Ward | 601/307 |

FOREIGN PATENT DOCUMENTS

| | | | |
|---|---|---|---|
| 1323319 | 7/1973 | United Kingdom | 128/155 |
| 2120104 | 11/1983 | United Kingdom | 128/156 |

OTHER PUBLICATIONS

Tip Stop-The Protection and Time-Savings you need, Medical Inc., Nov. 1990, 3 pages.

Primary Examiner—Randall L. Green
Assistant Examiner—K. M. Reichle
Attorney, Agent, or Firm—Barnard, Brown & Michaels

[57] ABSTRACT

A tape for attaching bandages, with non-adhesive tabs at each end for easy manipulation and removal while wearing gloves is disclosed. Also disclosed are tapes with target markings for location of a puncture wound, tapes with pressure disks or plates attached, and methods of making and using the tapes.

3 Claims, 4 Drawing Sheets

TEMPORARY BANDAGE TAPE

This application is a continuation-in-part of copending application Ser. No. 07/621,261, filed on Dec. 3, 1990, now U.S. Pat. No. 5,213,565.

BACKGROUND OF THE INVENTION

1. Field of the Invention

This invention relates to bandages and tapes, particularly to items used in a temporary fashion, such as in a hospital or dialysis situation, to stop bleeding in puncture wounds. It involves both temporary tapes which may be handled by those wearing gloves and tapes which provide guidance and assistance in applying pressure to a wound.

2. Description of the Related Art

In the past few years, in view of increasing health risks to practitioners in all areas of medicine, the use of rubber gloves has become routine. Furthermore, temporary tapes and bandages must be removed or changed frequently during many procedures. When one is wearing rubber gloves, however, the application and removal of tapes and bandages becomes a problem. The edges of the tapes are difficult to separate from the skin with a gloved hand, and the adhesive of the tapes sticks stubbornly to the gloves. Attempts to remove the used tape from the gloves often result in tearing or stretching the glove, which can defeat the very purpose of wearing the gloves in the first place.

For example, during kidney dialysis, or when blood is donated or received, needles and tubing must be taped to the patient's arm, and then removed; a bandage pad must be secured over the resulting wound until there is no longer a possibility of bleeding, and then it too is removed. During these procedures, the practitioners must wear gloves, due to the possibility of contamination from blood that is infected with hepatitis, the HIV virus, or other infectious agents. With the existing bandages and tapes, these procedures are difficult to accomplish while wearing gloves.

Up to this time, most of the development in this area has been focused on the separation of the tape from the backing which is used to protect the tape until it is used. For example, U.S. Pat. No. 4,807,613 (Koehnke) discloses a bandage in which non-adhesive tabs similar to those of the present invention are presented as a means for separating the bandage from its shield. Although the tabs of that invention may also allow for easier removal of the bandage from the skin if the adhesive used is not very strong, the perforations between the tabs and the adhesive part of the bandage present an undesirable possibility that the tabs will tear off of the bandage. In fact, this is presented as a feature of that invention, which is drawn to a more permanent bandage. The perforations of that invention also eliminate the possibility of placing the strips into a roll formation, with perforations between the strips to separate them from the rest of the roll. This is an important limitation, as a roll formation is particularly easy to use in a hospital or a similar setting where these tapes are used in large quantity (e.g., blood donation facilities). The roll eliminates the necessity for the gloved practitioner to remove individual packaging or a shield from each tape used.

One partial solution to this problem is to fold the end of the tape roll under onto itself, creating a non-adhesive tab. However, this maneuver, too, is difficult with a gloved hand, it must be repeated every time a piece of tape is used, and it creates only one tab end on each tape. In certain circumstances, it may be desirable to remove a tape by pulling in one direction particularly; however, with only one tab, the direction must be determined ahead of time, and the tape applied in the appropriate orientation for later removal.

Furthermore, at present, when blood is drawn from a patient, the puncture wound which results is stopped by placing a pad of multi-layered gauze over the wound and applying pressure thereon. Until a clot forms and bleeding is substantially stopped, continual pressure must be exerted against the wound to prevent loss of blood. Because the gauze pad which is placed on the wound is opaque, it is not possible to know the precise point at which to apply pressure. This is usually not a problem since under normal circumstances bleeding will stop in a matter of minutes as a clot forms over the wound.

In certain situations, however, a clot may take significantly longer to form. This can happen, for example, when a large needle is used, when an anticoagulant has been administered, or if the patient has poor clot-formation capabilities (e.g. if a patient is a hemophiliac). It is a particular problem in kidney dialysis, since a large needle is used and an anticoagulant is often administered. In some cases, pressure must be continually applied for as long as half an hour before a clot is sufficiently formed to stop most of the bleeding. In such a situation, it is important to apply pressure directly over the wound site in order to minimize blood loss over time.

One solution to this problem was proposed by the inventor in U.S. Pat. No. 4,981,133: a bandage pad with indicia on top and bottom, marking the place of the puncture wound. Also disclosed in that patent was a plastic piece, with a "nipple", which when placed over the bandage would provide concentrated pressure on the wound. However, the present invention combines a temporary tape particularly suitable for such applications with a marking system which is even better than those previously used.

SUMMARY OF THE INVENTION

By providing a temporary tape with non-adhesive ends and target indicia, as well as an optional pressure disk, the present invention solves all of the above-mentioned problems. The invention is a new style of tape for securing a bandage pad, which is easy to remove from a roll and from the skin by someone who is wearing gloves. The presence of permanently attached, non-adhesive tabs at both ends of a predetermined length of tape allows the tape to be easily removed by a medical practitioner who is wearing gloves, or by a patient who does not have the dexterity to peel a regular tape or bandage off the skin. The tapes may be stored in and dispensed from a roll, by separating the strips with perforated areas to allow for removal from the remainder of the roll, or in a pad.

The individual tapes may also have "target" indicia for marking the place of a puncture or other small wound. When used as disclosed herein, the tapes allow for improved placement of pressure on the wound. If the optional disk is included as part of the tape, the tape itself may provide the necessary pressure on the wound.

It is therefore an object of this invention to provide a style of surgical or bandage tape which is easily removed from the skin or from a roll or pad of similar tapes by someone wearing gloves.

It is a further object of this invention to provide a temporary tape or bandage which may be easily removed from the skin by a patient with limited dexterity.

It is yet a further object of the invention to provide a system for packaging tapes or bandages of a predetermined lengths, with non-adhesive areas at each end, such that the tapes or bandages are easily removed from said packaging by one who is wearing gloves.

It is yet a further objective of the invention to provide an improved mechanism for marking the place of a wound requiring pressure.

It is yet a further objective of the invention to provide a simple means for holding a bandage, marking a wound, and providing pressure on the wound.

These and other objectives, features, and advantages of the present invention may be found in the following description, drawings, and claims.

DETAILED DESCRIPTION OF THE INVENTION

Figure 1:
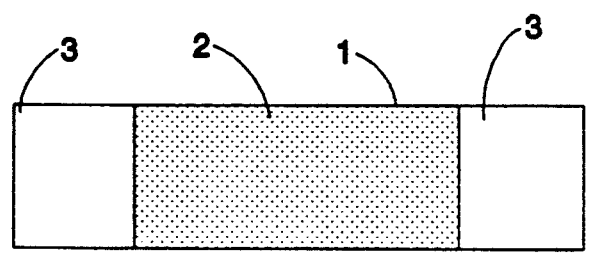
FIG. 1 is a bottom (adhesive side) view of a single tape with non-adhesive ends.

This invention includes a new style of tape which is easily handled by those wearing gloves. It has a middle section (1) with adhesive on one surface (2), and two end sections (3) having no adhesive on either surface (see FIG. 1). one end section is fixedly attached to each end of the middle section. The tape may be of any length or width, may be made of any material which is sufficiently flexible to conform to the contours of the human body, e.g., rubber, cloth, paper, or flexible plastic, and may be packaged individually or in a roll or pad formation. The end sections (3) should be long enough that they may be gripped by a gloved hand, as shown in FIG. 4, without the glove coming into contact with the middle section (1) of the tape.

Figure 2:
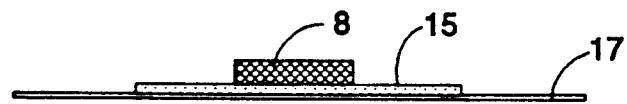
FIG. 2 is a side view of a single bandage with non-adhesive ends, made by applying adhesive to one portion of a non-adhesive tape, and applying an absorbant pad to the adhesive section.
Figure 3:
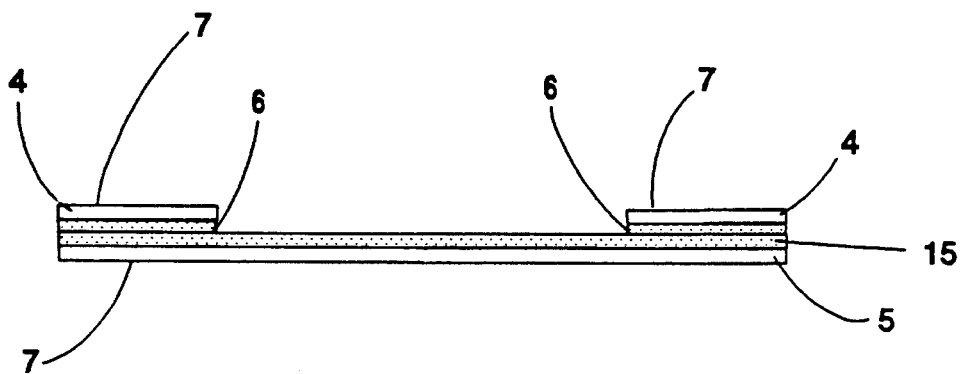
FIG. 3 is a side view of a single tape with non-adhesive ends, made by joining a piece of tape to separate tab pieces.

These tapes may be made in many ways. A single tape may be made by applying adhesive (15) to only one portion of a piece of non-adhesive tape (17), as in FIG. 2, or by applying short tab pieces (4) of backing material to the ends of a longer piece of tape (5) which has adhesive (15) on one side (FIG. 3). The backing material may be non-adhesive material, or -material which is adhesive on one side. If an adhesive material is desired, the same tape that is used for the long piece may also be used as a backing material, or a different material may be selected. If such adhesive material is used, it is placed onto the main tape (5) such that the adhesive sides of the tape and the backing material come together (6), creating non-adhesive outer surfaces (7) on both sides. The use of adhesive backing material for the tabs creates a firmer bond between the adhesive surfaces of the tape and the tabs, with less likelihood that the backing material will become separated from the tape, which would defeat the purpose of the tabs.

A bandage may be made by applying an absorbent pad (8) (made of gauze, cloth, or any absorbent material) to a tape made by any of the methods outlined above, or by joining such a pad between two pieces of tape that each have a single non-adhesive end, such that these non-adhesive ends are distal to the pad.

Figure 4:
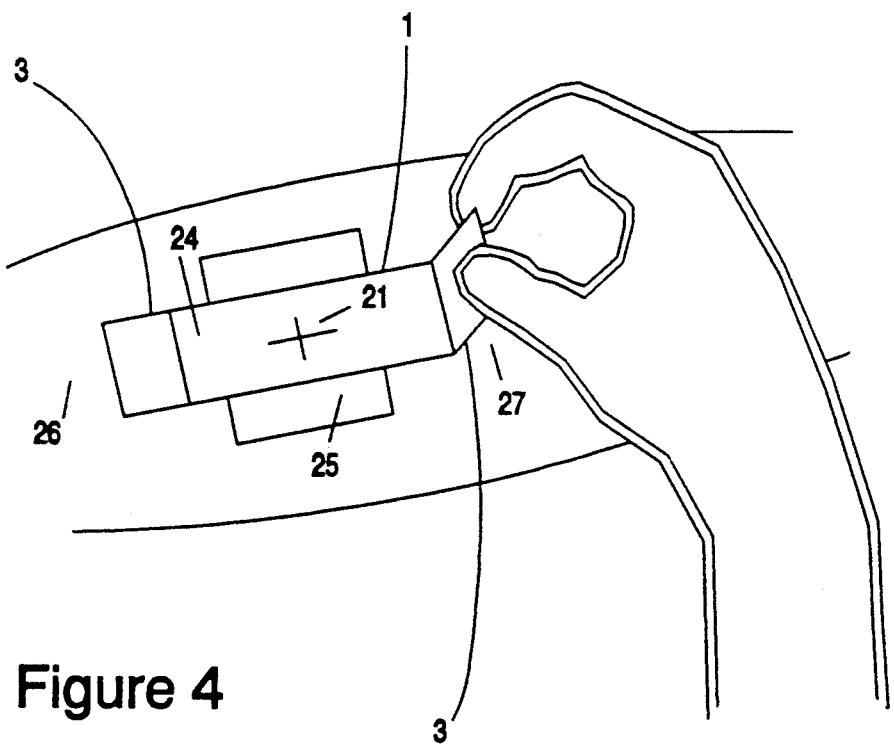
FIG. 4 shows a tape with non-adhesive ends and target indicia, in place on a patient's arm, and demonstrates removal of such tape from the skin by a gloved hand.

A tape like that described above may be further modified by the addition of a target marking of some sort for indication of the position of a wound beneath a bandage (See FIG. 4). This sort of tape is most useful if it is made of a transparent or translucent material. The target marking may be in the form of a dot, circle, concentric circles (a "bullseye"), crosshairs, or any other diagrammatic means of indicating a particular place on the tape. A tape with such markings is used as follows (see FIG. 4): the tape is aligned above the skin so that the markings (21) are directly over the wound, the adhesive section of one end of the tape (24) is attached to the skin (26) beside the wound, a bandage pad (25) is placed over the wound, and then the remainder of the tape is placed across the bandage pad and affixed to the skin on the other side of the pad (27). If a needle has not yet been removed from the wound, it may be removed at this point. The target (21) will mark the optimum spot for applying pressure to stop the bleeding, even though the wound itself is not visible through the pad.

The markings on the tape have several advantages over similar markings on a bandage pad (as disclosed in U.S. Pat. No. 4,981,133). First, the tape may be made transparent, allowing for easier alignment of the marking with the wound. Second, the tape is affixed, by means of adhesive, directly to the skin, and it is not as likely to slip from its initial placement as is a bandage pad. Third, if a dye or similar substance is used to make the marking, it is much less likely that such dye will move, even when wet, from the tape to the skin; if the dye is in the pad itself, it is more likely to seep to the skin and cause adverse effects.

Figure 7:
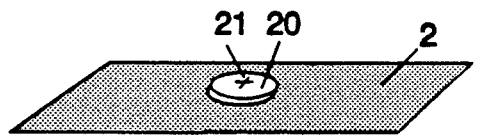
FIG. 7 shows a tape with a plastic pressure disk which has target markings in the form of cross-hairs.
Figure 8:
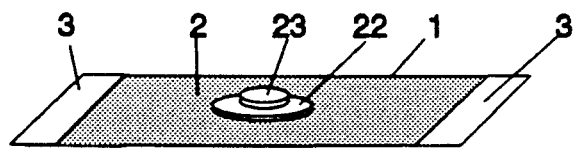
FIG. 8 shows a tape with non-adhesive ends and a pressure disk of another type.

Another possible modification of the tape is the addition of a pressure disk or plate of some sort, to provide additional pressure to a certain part of the area covered by the tape. For example, a disk may be cut or formed from a rigid material (e.g., plastic), and attached to the adhesive side of the tape. In one embodiment, a disk made of Lucite TM, having a diameter of approximately ½" and a thickness of approximately ¼", is attached to the center of the tape. FIG. 7 shows a tape with a pressure disk of this type (20), which also has a target marking (21). Another type of disk is shown in FIG. 8, on a tape with non-adhesive ends. This disk has one layer, about 1" to 1.5" in diameter (22), with a smaller disk (approximately ½" diameter) (23) attached in the center of the first disk. When a tape with this type of disk is placed over a wound, with the disk toward the skin or bandage pad, the pressure of the tape on the large disk will be transferred and concentrated into the area covered by the smaller disk, providing increased pressure on the wound.

These disks may be used in combination with target markings, as in FIG. 7; note, however, that the disk itself may serve as a marking, or the presence of the disk may render a target unnecessary, since the disk may provide enough pressure against the wound to eliminate the need for manual pressure.

Although the combination of non-adhesive ends with target markings and/or a pressure disk provides many advantages in one product, these devices (non-adhesive ends, target markings, and pressure disks) may be used singly or in combination. Each provides an improvement in tapes for use in a hospital, dialysis, or blood-donation setting. For example, as shown in FIG. 7, a tape without non-adhesive ends can be made with a target, a disk, or both; this sort of tape may be useful in a more permanent situation, when the non-adhesive ends would be an annoyance. A plain tape, or one with target markings, may also be used with a bandage pad that has a pressure disk affixed thereto.

Figure 5:
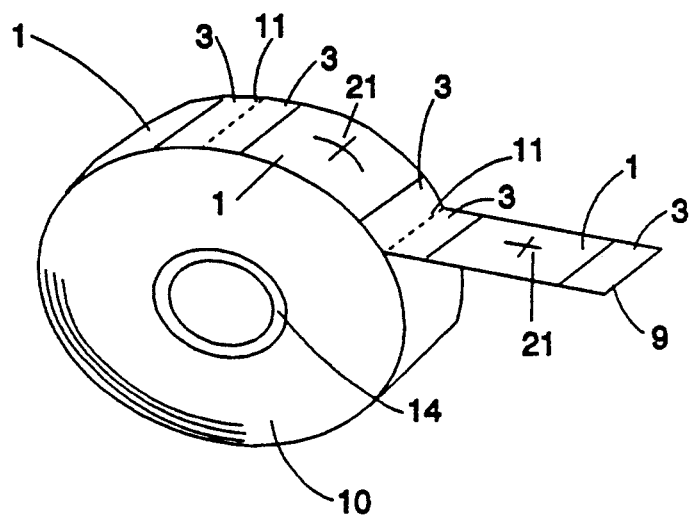
FIG. 5 shows a roll of tapes with non-adhesive ends and target markings in the form of crosshairs.

The tapes, with or without target markings and with or without pressure disks, may be individually packaged or placed into a roll, with the individual pieces separated from each other by perforations for easy removal from the roll. See FIG. 5. The free end (9) of the roll (10) will have a non-adhesive tab (3) which may be gripped to pull the next tape from the roll. The tape may be removed from the roll by a sharp tug, which will tear the tape at the perforations (11). This procedure may be performed with or without gloves, and the tape will not stick to the gloves.

Figure 6:
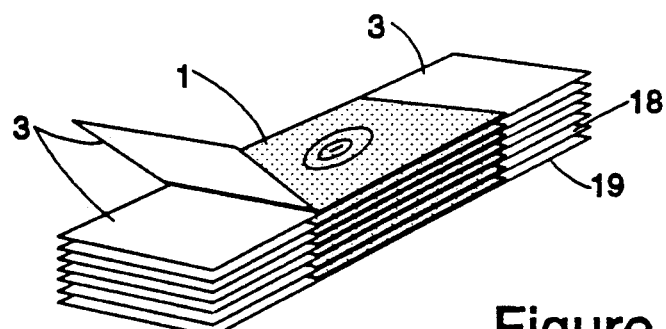
FIG. 6 shows a pad of tapes with non-adhesive ends and target markings in the form of a bullseye.

The tapes may also be packaged in a pad formation, as shown in FIG. 6, wherein the adhesive side of each tape is attached to the non-adhesive side of the tape below it. The bottom-most tape (18) may be placed onto a heavy backing material (19), such as cardboard. The non-adhesive tabs (3) allow the tapes to be removed from the pad for individual use.

A roll of the tapes may be made by a manufacturing process whereby a length of tape of the desired width is fed along a path, with the adhesive side down and the non-adhesive side up, and a length of backing material is fed in a path perpendicular to and underneath the first length. If the backing material has an adhesive side, it must be fed with the adhesive side up and the non-adhesive side down. The tape is advanced along its path to the desired length, the tape and the backing material are brought together, and a sharp blade is used to cut the backing material at the edges of the tape, creating an area on the tape which has backing attached. If an adhesive backing is used, this area will have adhesive in the middle, between the two materials, but none on either exposed surface. A perforating device can then be used to perforate the tape and backing in the center of this non-adhesive area. Markings and/or pressure disks may then be applied to the tape. The tape, with non-adhesive sections (provided by the backing material) and perforations, can then be wound onto a roll (14).

By grasping the non-adhesive tab at either end of the tape (see FIG. 4), one may easily remove the tape from the roll or pad, and later from the skin of a patient, even when wearing gloves.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

What is claimed is:

1. A roll of tapes with non-adhesive ends which may be used by a gloved person, comprising:
    a) a center spool,
    b) a length of tape wound around said spool, said tape comprising repeating segments, each of said segments comprising:
        1) a first non-adhesive section, having non-adhesive surfaces on both sides thereof,
        2) a second non-adhesive section, having non-adhesive surfaces on both sides thereof, and
        3) an adhesive section, having an adhesive surface on one side thereof and a non-adhesive surface on the other side thereof, disposed between said first non-adhesive section and said second non-adhesive section such that said adhesive surface covers the entire area on the one side of said adhesive section between said first non-adhesive section and said second non-adhesive section, and is permanently attached to said first and second non-adhesive sections,
    whereby each of said repeating segments is attached to at least one other of said repeating segments, in an end-to-end manner, with a perforated attachment between segments; wherein the non-adhesive sections of each of said segments are of sufficient size to enable said gloved person to grasp one of said non-adhesive sections using a hand covered by a glove, without having said glove come into contact with the adhesive surface of the adhesive section of said segment, and wherein said sections are transparent.

2. The roll of claim 1, wherein the adhesive section of each of said repeating segments further comprises a target for marking the exact spot of a wound.

3. The roll of claim 2, wherein said target is in the form of an "X".

* * * * *